United States Patent [19]

Mercer et al.

[11] 4,242,292
[45] Dec. 30, 1980

[54] METHOD FOR EMBEDDING THREADED APERTURED BUTTON IN BASE OF DENTAL CAST

[76] Inventors: Roger W. Mercer, 1340 Arlington Dr., Fairborn, Ohio 45324; Louis E. Hay, 847 Woodhill Rd., Dayton, Ohio 45431

[21] Appl. No.: 28,536

[22] Filed: Apr. 9, 1979

Related U.S. Application Data

[62] Division of Ser. No. 788,236, Apr. 18, 1977.

[51] Int. Cl.³ .......................... B29C 5/00; B29D 3/00
[52] U.S. Cl. .................... 264/16; 264/138; 264/249; 264/274; 264/278
[58] Field of Search ............. 264/261, 16–20, 264/262, 318, 138, 249, 278, 274; 32/32; 29/458, 460, 536 R; 52/704, 707, 743; 433/54, 60

[56] References Cited

U.S. PATENT DOCUMENTS

| | | | |
|---|---|---|---|
| 809,177 | 1/1906 | Drolshagen | 52/704 |
| 1,815,956 | 7/1931 | Ralph | 32/32 |
| 2,119,579 | 6/1938 | Hagman et al. | 32/32 |
| 2,167,176 | 7/1939 | Grassberger | 85/32 V |
| 2,438,725 | 3/1948 | Tamarin | 32/15 |
| 2,592,288 | 4/1952 | Johnson | 32/32 |
| 2,629,929 | 3/1953 | Levine et al. | 32/32 |
| 2,644,233 | 7/1953 | Schmukler et al. | 32/32 |
| 2,659,145 | 11/1953 | Gillman | 32/15 |
| 2,880,830 | 9/1959 | Rohe | 52/704 |
| 2,909,806 | 10/1959 | Cheythey | 156/293 |
| 3,271,498 | 9/1966 | Rohe et al. | 264/261 |
| 3,653,126 | 4/1972 | Hansen | 32/32 |
| 3,842,877 | 10/1974 | Andrews | 85/32 V |
| 3,913,230 | 10/1975 | Weiss | 32/32 |
| 3,919,774 | 11/1975 | Fishman | 32/15 |

OTHER PUBLICATIONS

Delmonte, Technology of Adhesives, Reinhold, N. Y. (1947), pp. 477 & 478.
Katz, Adhesive Materials, Foster Pub. Co., Long Beach, Ca. (1964), p. 87.

*Primary Examiner*—W. E. Hoag

[57] ABSTRACT

A novel method for embedding a button into a dental cast by forming a cavity and pouring a cold setting material such as a plastic into which a screw is inserted while the poured button is in the fluid form before final setting. The screw has a notch in at least one thread so that the molding material forms an interlock or detent in the notch, which is sheared upon removal of the screw.

5 Claims, 13 Drawing Figures

METHOD FOR EMBEDDING THREADED APERTURED BUTTON IN BASE OF DENTAL CAST

REFERENCE TO RELATED APPLICATION

This is a divisional application of co-pending application Ser. No. 788,236 Apparatus and Method For Mounting Dental Casts, filed Apr. 18, 1977.

REFERENCE TO RELATED U.S. PATENT

U.S. Pat. No. 3,975,489 Cast Ejector, relating to a method of embedding a precast plastic button into a dental cast.

BACKGROUND OF THE INVENTION

Dental articulators are a common and necessary apparatus in the fabrication of a dental prosthesis. Stripped to its bare essentials, the process of fabricating a prosthesis commences when the dentist takes impressions of the patient's maxillary and mandibular arches which may or may not include natural teeth. These impressions are negative imprints of the arches and become the molds into which the raw material for forming positive casts is poured. These positive casts are duplicates of the patient's arches (with or without teeth) and become the primary model to which the prosthesis is to be constructed.

In order to construct an acceptable prosthesis, these dental casts are normally mounted in a dental articulator in order that the maxillary and mandibular casts are maintained in the same relationship as in the mouth of the patient. This is true in all cases even those where only one prosthesis, as for example the maxillary arch is to be constructed, since the prosthesis must also conform with the relating surfaces on the mandibular arch in the patient's mouth.

Another reason why the dental casts are mounted in an articulator is to permit arrangement of the denture (false) teeth in their proper position for occlusion. On partial dentures, the occlusion of the denture teeth must be with natural teeth. On full dentures, greater liberty is often taken to improve function and asthetics. The desired occlusion not only includes the vertical bite but also a degree of lateral movement as well as posterior and anterior movement of the lower jaw. These various movements are produced by the temporomandibular joint which is the joint formed by the condyle of the mandible and the temporal bone. Many dental articulators are built to simulate these movements to a high degree.

Past practice for countless years has been to mount the dental casts in the articulator by means of plaster which is usually a gypsum material. This locates the dental casts in a fixed position. Mounting the dental casts by means of plaster is relatively expensive, is dusty and time consuming because the powdered raw material must be thoroughly mixed with a liquid and the plaster must be allowed to set, the process is subject to error which cannot be compensated, and all utensiles must be thoroughly cleaned after each used. Even in cases where the dental casts have been provided with grooves to facilitate removal and replacement which is often a requirement in the fabrication process, it is very questionable at best whether or not the casts were replaced in their original mounted position.

At least 95% of all dental articulators built to date have been built for use with plaster mounting techniques. A few have been built which use mechanical mounting devices such as claws or other clamping devices in an attempt to find a better mounting technique than by the use of plaster. These alternate mounting techniques have been far less satisfactory than plaster, especially in those situations where the dental casts are to be removed and remounted to their original positions.

As will be shown, the new apparatus and mounting techniques of the present invention, introduce an entirely new concept for the mounting of dental casts which is cheaper, faster and more accurate than prior methods.

SUMMARY OF THE INVENTION

The single feature of the present invention which makes all other features of enhanced value is the mounting of the dental casts by means of a screw thread engaging a threaded button embedded in the base of each cast. The button may be embedded at the time the cast is poured in accordance with the teachings of U.S. Pat. No. 3,975,489; or, the button may be embedded in accordance with the present invention. A button embedded in accordance with U.S. Pat. No. 3,975,389 must be embedded at the time the cast is poured; whereas, a button in accordance with the present invention may be embedded at any time after the cast has hardened. The new method is especially valuable in a situation where the cast was poured without a button, or in a situation where the embedded button was not located at its most desirable location on the dental cast; that is to say, a new button may be embedded at any time. A poured button may be formed with tools and raw materials available in every dental laboratory.

The apparatus of the present invention, which will be called a mounting jig, may be adapted to be mounted onto some existing dental articulators; However, in most cases it will be preferable to build a new articulator having increased height between the base and the upper pivoted leaf in order to better accomodate the new mounting jigs. The new articulator should also be provided with feet on the base in order to provide clearance for portions of the jig which extend below the base. Another reason for a new articulator is because nearly all present articulators were built to have lathlike configurations for holding plaster, whereas plane surfaces are now preferable. The new articulator may be made with the same condylar movements (if any) as previously, since the new mounting methods and movements of the several mounting jigs are independent of such condylar movements.

Mounting jigs in accordance with the present invention can be provided with a number of independent adjustments which cannot be attained when dental casts are mounted in a conventional articulator by use of plaster. The most common and often used adjustment is the vertical adjustment which can take several forms, as for example, by screw means or by sliding rods between several elements of the jig. The jig may also be provided with adjusting means permitting anterior-posterior movement as well as lateral movement of one dental cast in relationship with the other cast.

In addition to the above mentioned adjustments, one form of the mounting jig provides an adjustable wobble plate which will cant to an infinate number of positions as may be required to bring opposing mounted dental casts into proper occlusion. Several methods of building the wobble plate were tried. A universal joint type of mount gave satisfactory canting movement; however, a ball socket mount is found to be preferable because by using a split socket which could be tightened, it was found that a mounted dental cast could also be rotated, after which the split socket is tightened against the ball to maintain the rotational adjustment.

The various adjustments were found to be of great value in situations where the buttons were embedded in the dental casts by the method of U.S. Pat. No. 3,975,489 and the two buttons were not on a common vertical axis when the two casts were in proper occlusion. The various adjustments described above permit perfect adjustment to required occlusion position. As will be shown in the Preferred Embodiment of the Invention, nearly all adjustment means are also provided with scales. The various scale settings when the casts are in proper occlusion may be recorded. If a particular pair of matched casts are removed and other casts are mounted and aligned in the articulator, the first pair of casts may be subsequently remounted to their original alignment by setting the various adjustments to their recorded scale positions.

The alignment problem has been nearly eliminated when at least one of the embedded buttons is installed by the new method of the present invention. This is accomplished by the ability to embed the button in the second cast into vertical alignment with the embedded button in the first cast while the two casts are in their occlusion position. This method and several other novel features will be described in greater detail in the Preferred Embodiment of the Invention.

DESCRIPTION OF THE PREFERRED EMBODIMENT

Figure 1:
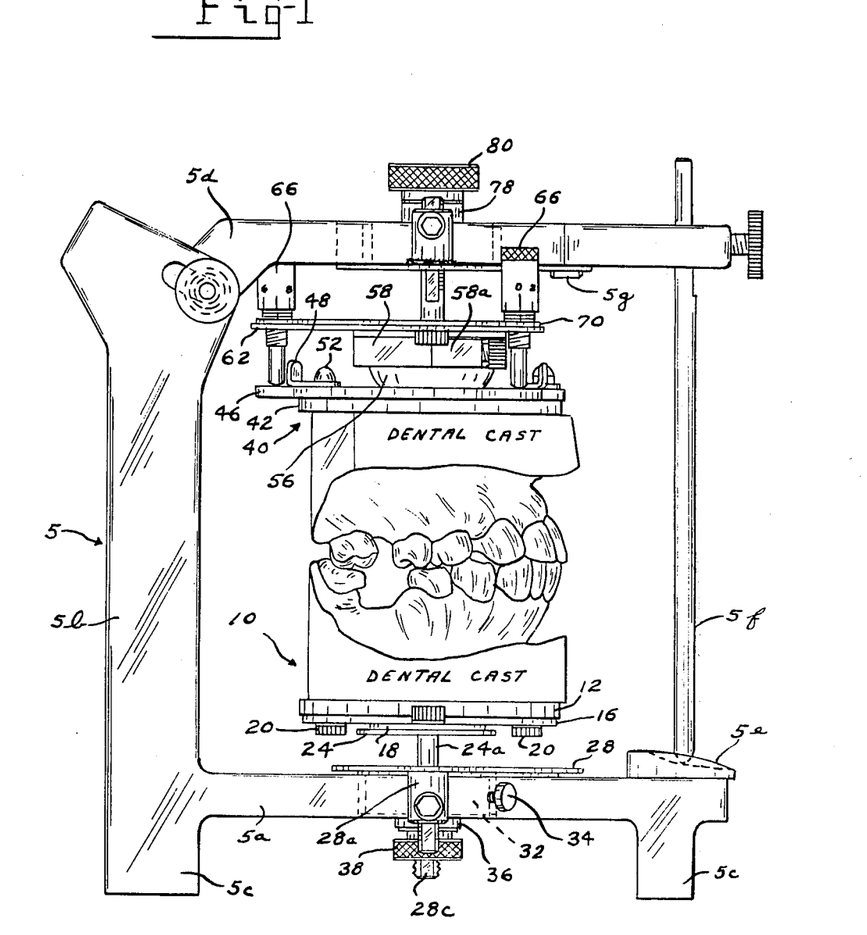
FIG. 1 is a side elevation view of a dental articulator supporting an upper and a lower mounting jig to which a matched set of dental casts are attached and held in their occlusion position.
Figure 2:
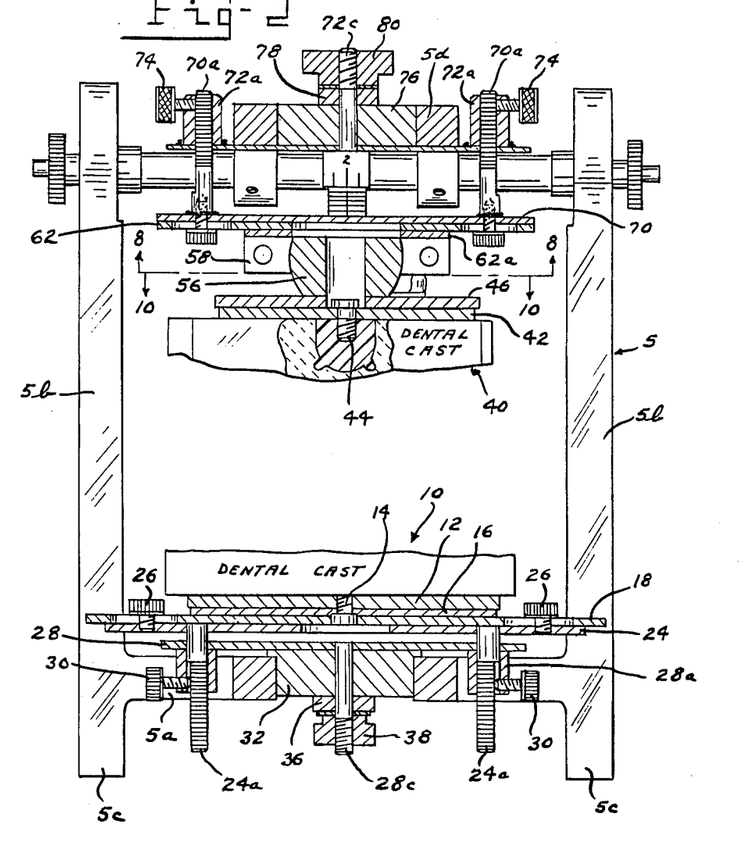
FIG. 2 is a front elevation comparable to FIG. 1 with the dental casts broken away and showing the mounting jigs in section.

At the onset it should be noted that both the upper and the lower mounting jigs depicted in FIGS. 1 and 2 have anterior-posterior movement and also have lateral movement. Both mounting jigs also have the same vertical movements. The difference in configuration is due to the addition of a ball socket supported wobble plate on the upper mounting jig.

It should also be noted for a better understanding from the beginning that it is not necessary to use the combination of jigs as depicted. Dependent on personal preference or the laboratory functions to be performed, the jigs may be reversed; i.e., the upper mounting jig may be mounted on the base of the articulator and the lower mounting jig may be mounted on the leaf of the articulator. If desired, both jigs may also be either as the upper depicted mounting jig, or both jigs may be as the lower depicted jig.

Figure 13:
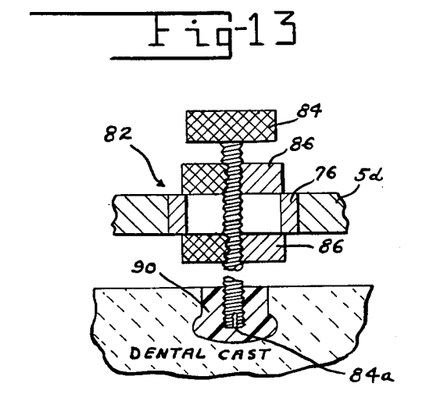

As will be fully developed below, there are also situations in which a simple mounting jig as depicted in FIG. 13 will suffice. The element in common is that in all situations the dental casts are mounted to the jig by a screw means engaging the thread of a button embedded in the base of the dental casts.

Specific reference is made to FIGS. 1 and 2 which depict two forms of a mounting jig joined to a suitable dental articulator 5. The articulator has a horizontal base 5a, two vertical upright members 5b, a plurality of suitable feet 5c providing clearance for portions of the mounting jig which extend below the base, and a pivoted leaf 5d which is pivotally joined to the upper ends of the upright members 5b and has a normally horizontal position superimposed above the base.

The element of each mounting jig which directly engages the articulator and is slotted for anterior-posterior movement may be made integral or detachable with the base and leaf of the articulator within the scope of the present invention. Many articulators are made of die castings and it is obvious that an elongated slot may be cast or machined into the die casting. However, it is preferable that the slotted element be made of a harder material, such as steel, and that it be inserted into the die cast elements by direct casting into position, by interference fit, or by retaining means such as screws, pins or other means well known to the art. Such retaining means may be more or less "semi-permanent" as by drive pins or recessed set screws with a lock screw; or, the retaining means may be of the "quick-disconnect" type. For purposes of illustration, a "quick-disconnect" type of retaining means is shown; however, within the scope of the present invention, all that is necessary is to provide slots which will permit horizontal movement of the remaining elements of the mounting jig.

The mounting jigs illustrated in FIGS. 1 and 2 have anterior-posterior movement and also lateral movement. Although the slotted element carried by the base and the leaf are illustrated to have an anterior-posterior slot and the lateral movement is in other elements of the mounting jig, it is obvious that within the scope of the invention, these movements may be reversed; i.e., the slots in the base and leaf may be positioned to provide lateral movement and other elements of the mounting jigs would provide anterior-posterior movement. The particular arrangement illustrated was selected for ease of operation since all adjustments can be made from the front of the articulator.

The leaf 5d may be pivoted in any conventional manner; many types of pivots being known and used in the dental art. The articulator is also provided with an incisal table 5e and an incisal guidance pin 5f whose functions are well known to the art.

Figure 5:
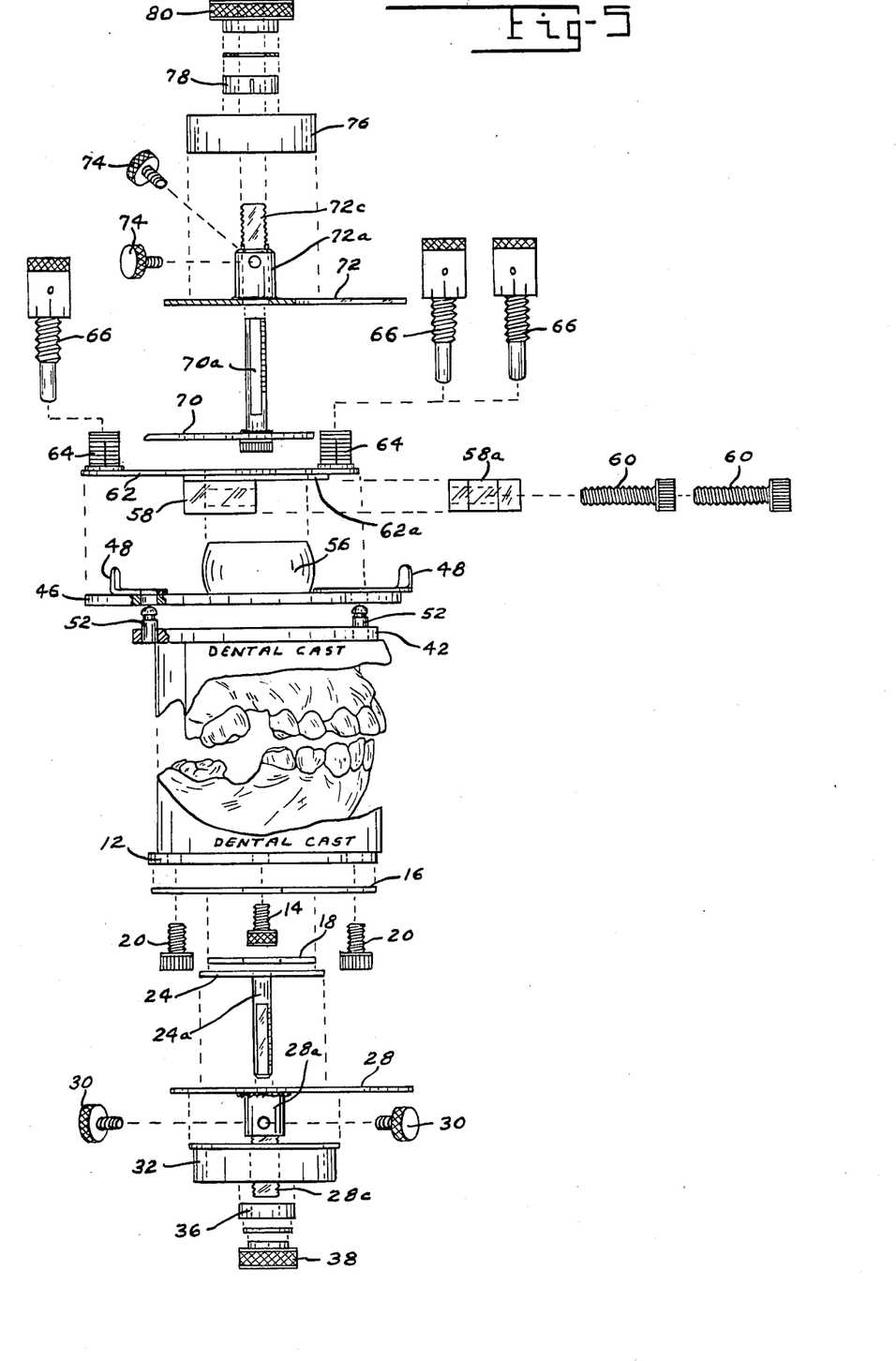
FIG. 5 is an exploded elevation of the upper and lower mounting jigs removed from the articulator.
Figure 6:
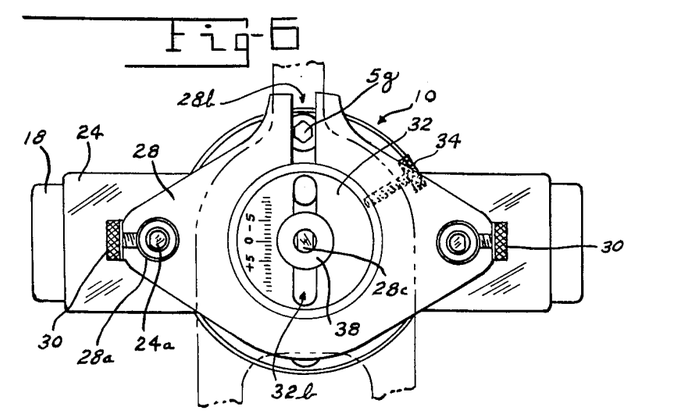
FIG. 6 is a bottom plan view taken along the line 6—6 on FIG. 3 and showing in particular the anterior-posterior movement of the mounting jig.
Figure 7:
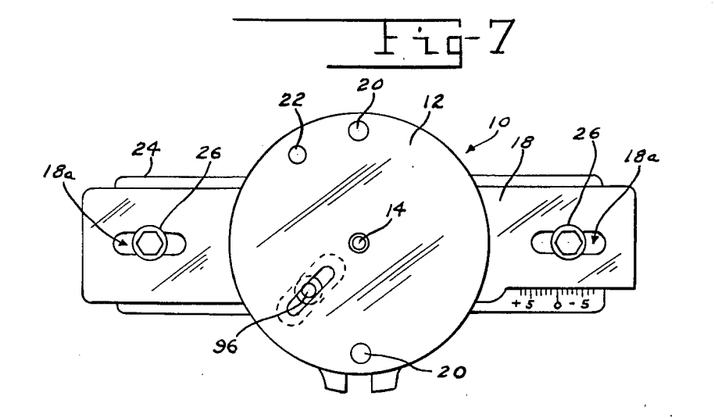
FIG. 7 is a plan view of the lower mounting jig taken along the line 7—7 of FIG. 3 and showing lateral movability.

The lower mounting jig 10, a plan view of which is shown in FIG. 7 and a lower plan view of which is shown in FIG. 6, has a dental cast plate 12 to which a dental cast may be mounted by means of a screw 14 which is centrally located as best shown in FIG. 5 and FIG. 7. The screw 14 engages an embedded button, as for example, a button embedded in accordance with U.S. Pat. No. 3,975,489. The button may also be embedded in accordance with the present invention; the precise embedding procedure to be fully described below.

The cast plate 12 is detachably mounted to a support plate 16 which is permanently attached to the top side of lateral slide member 18 by means of rivets, spot welding or other suitable method of joining. The support plate 16 is of the same peripheral configuration as the cast plate 12 and the two are detachably joined by screws 20 as best shown in FIG. 5 and FIG. 7.

The head of the screw 14 which holds the dental cast in position on the cast plate 12 enters a centrally located guide hole in the support plate 16 and thereby establishes a common center location for the cast plate 12 and the support plate 16. Rotational alignment is provided by a locating pin 22 which is shown only in FIG. 7. The locating pin 22 is permanently attached to the cast plate 12 and slidably engages a hole in the support plate 16. It is thus noted that the cast plate may be repeatedly detached and reattached to the same predetermined position on the support plate. It is important that this position is maintainable in situations where the dental cast and the cast plate 12 must be removable as a unit during the course of fabricating some types of a prosthesis.

The lateral slide member 18 is superimposed on the vertical rise plate 24 where it is held in place by screws 26. As best shown in FIG. 7 the lateral slide member 18 is provided with two elongated slots 18a which permit lateral movement of slide member 18 relative to the vertical rise plate 24 when screws 26 are loosened. As will be shown, although the vertical rise plate 24 has vertical movement, it cannot move laterally. As best shown in FIG. 7 a convenient scale is scribed onto the vertical rise plate to indicate the right or left lateral displacement of screw 14 from the vertical axis of the articulator. An index line (not shown) is scribed on the edge of the lateral slide member adjacent to the scale, the index line being located to read 0 on the scale when the screw 14 is on the vertical axis of the articulator. Since the dental cast moves with the lateral slide member 18, moving the lateral slide member moves the lateral position of the dental cast in relation to the vertical axis of the articulator.

The subassembly comprising cast plate 12, support plate 16, lateral slide member 18 and vertical rise plate 24 is superimposed over base plate 28. The base plate is provided with two permanently attached guide sleeves 28a which slidably engage vertical rise plate pins 24a. The above defined subassembly may be manually positioned and held in place by means of screws 30. As best illustrated in FIG. 2, the vertical rise plate pins 24a are scribed with a scale which may be read by using the bottom of guide sleeves 28a as the scale index. The base plate 28 is provided with a slot 28b which slidably engages a guide pin 5g on the articulator as shown in FIG. 6. It is noted that the vertical adjustment does not in any way affect the lateral adjustment.

Figure 3:
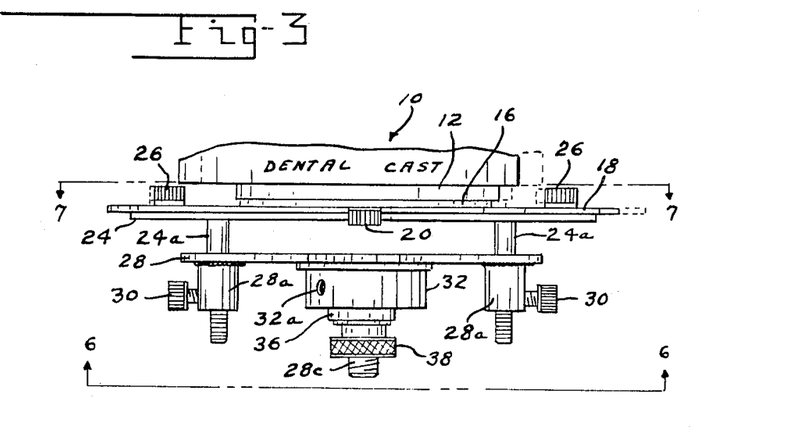
FIG. 3 is a front elevation of the lower mounting jig removed from the articulator.
Figure 4:
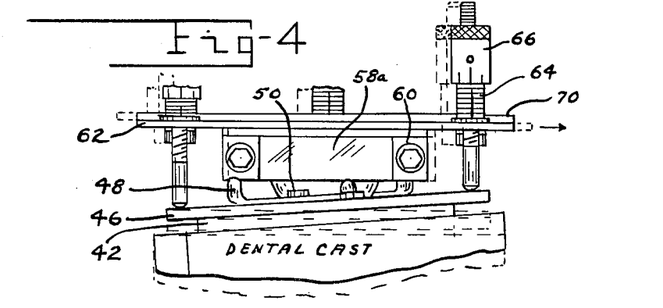
FIG. 4 is a front elevation of the lower portion of the upper mounting jig with the wobble plate canted, and indicating lateral movability by phantom lines and arrow.

A mounting ring 32 is detachably retained within a bore through the base on the vertical axis of the articulator by means of a retaining means such as screw 34 which engages a detent 32a as shown in FIG. 3 in order to hold the mounting ring in place without rotation. The screw retaining means is shown for simplicity of illustration only; there being better retaining means such as cam locks which are far more difficult to illustrate. No novelty is claimed for the retention means to be used.

Referring specifically to FIG. 6, the mounting ring 32 is provided with an elongated slot 32b which slidably receives threaded retaining pin 28c which is centrally and permanently attached to the underside of base plate 28 so that in its normal position it will be on the vertical axis of the articulator. The sides of the retaining pin 28c are milled as shown to provide better bearing surfaces in the elongated slot 32b and to prevent rotation of the jig in the mounting ring 32. As shown in FIG. 6, a scale is cut to be parallel with the elongated slot and having the 0 position on the vertical axis of the articulator.

A washer 36 having flat sides (best shown in FIGS. 2 and 5) slidably engaging the flat sides of retaining pin 28c is placed on the retaining pin to be adjacent to the scale. A vertical scribe line is cut on the periphery of washer 36 so as to be on the 0 position on the scale when the retaining pin is on the vertical axis of the articulator. The entire assembly is held in place by knurled nut 38.

When the knurled nut 38 is loosened, the entire lower mounting jig (less mounting ring 32) may be moved in the anterior-posterior direction completely independent of the vertical and lateral movements which were previously described. The purpose of the slot 28b and guide pin 5g as shown in FIG. 6 is to guide the anterior-posterior movement and to prevent any slight rotational movement of the assembly in the articulator.

The lower mounting jig 10 which has been described may be removed from the articulator by loosening the retainer screw 34 and lifting the entire assembly from the articulator; or, it may be removed by removing the knurled nut 38 and removing the assembly (less mounting ring 32) from the articulator. Since the mounting ring performs a necessary function relating to the anterior-posterior movement, it is obvious that within the scope of the present invention, the slotted mounting ring may be made detachable as shown, or it may be made integral with the base of the articulator.

Figure 9:
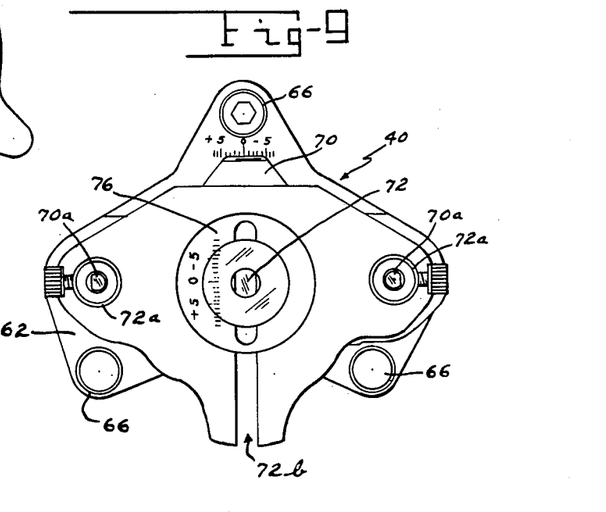
FIG. 9 is a plan view of the upper mounting jig showing anterior-posterior movement and the scales for reading both the anterior-posterior and the lateral movements.

The upper mounting jig 40 is depicted in its assembled position in FIGS. 1 and 2. A plan view of the assembly is shown in FIG. 9. In addition to performing the same independent vertical, lateral and anterior-posterior functions which are performed by the lower mounting jig 10, the upper mounting jig 40 performs a canting function, the requirement for which will be explained below.

Figure 11:
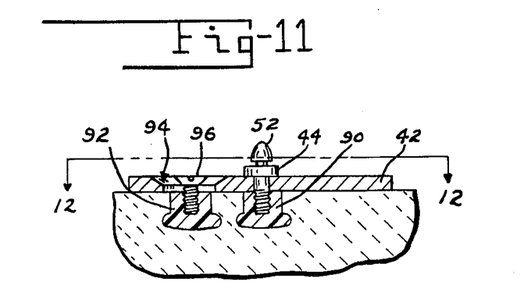
FIG. 11 is a section of the upper cast plate attached to a dental cast by means of screws engaging buttons embedded in accordance with the present invention.
Figure 12:
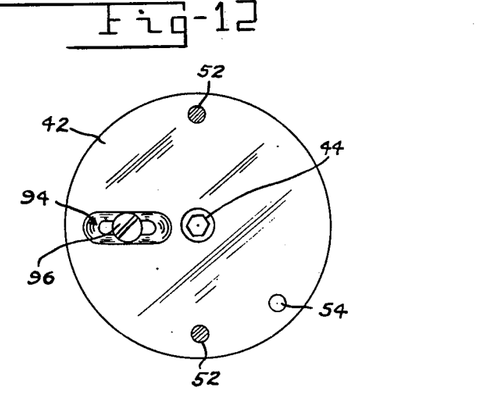
FIG. 12 is a plan view taken along line 12—12 of FIG. 11 and showing the screws joining the cast to the upper cast plate; and, FIG. 13 is a partial section showing a third form of the mounting jig supporting a dental cast having a button embedded in accordance with the present invention.

The upper mounting jig 40 has a dental cast plate 42 to which a dental cast may be mounted by means of a screw 44 which is centrally located as best shown on FIGS. 11 and 12. The screw 44 engages an embedded button, as for example, a button embedded in accordance with U.S. Pat. No. 3,975,489. The button may also be embedded in accordance with the present invention, the precise embedding procedure to be fully described below.

Figure 10:
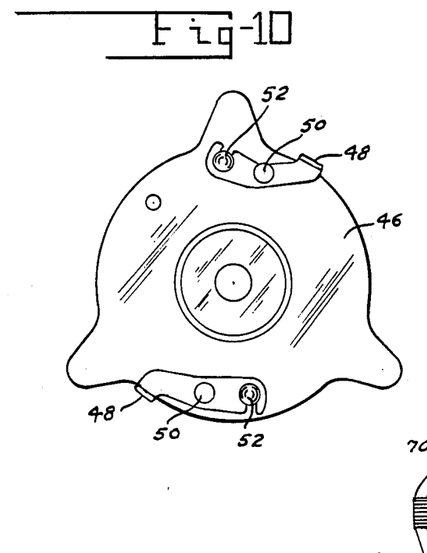
FIG. 10 is a plan view taken along the line 10—10 on FIG. 2 and showing the cast plate latched to the wobble plate.

The cast plate 42 is detachably mounted to a wobble plate 46 by means of two latches 48 which are pivotally joined to move on the upper face of the wobble plate by pivot pins 50 as shown in FIG. 10. The latches engage with latch pins 52 which are permanently attached to the cast plate 42 and extend upward through apertures in the wobble plate 46. If desired, the cast plate may be detachably joined to the wobble plate by means of screws, as for example, in the manner screws 20 join cast plate 12 to the support plate 16 on the lower mounting jig 10. In like manner, within the scope of the present invention, the cast plate of the lower mounting jig may be detachably joined by means of latches as are shown on the upper mounting jig. The latches and the screws perform the same function.

Rotational alignment of the cast plate 42 is provided by a locating pin 54 which is shown only in FIG. 12. The locating pin is permanently attached to the cast plate 42 and slidably engages an aperture in the wobble plate 46.

The wobble plate is pivotally supported by a ball socket arrangement in which the ball 56 is centrally attached to the upper face of the wobble plate, and the socket comprises a fixed portion 58 and a cap portion 58a which are held together by means of screws 60. The ball may be joined to the wobble plate by means of flat head screws from the bottom of the wobble plate (not shown). As best shown in FIG. 2 the ball has a vertical passage therethrough to provide clearance for the head of screw 44. As also shown in FIG. 2 and FIG. 5, the top and bottom of the ball were cut off to conserve vertical space in the articulator.

The fixed portion 58 of the socket is permanently affixed to the lateral slide 62 by means of rivets (not shown). A shim 62a was placed between the fixed portion 58 of the socket and the lateral slide 62. As best shown in FIG. 2 the lateral slide 62 and the shim 62a have apertures to provide clearance for the ball when it cants in the socket.

The lateral slide 62 has three internally threaded posts 64 affixed, two of which are best shown in FIG. 5. Adjusting screws 66, as best depicted in FIG. 5 engage the threaded posts 66 and extend through to contact the top surface of the wobble plate 46. The upper end of each adjusting screw is built like the thimble on a micrometer; i.e., the thimble surrounds the post. The thimbles and the posts are graduated with scales such as are found on a micrometer, with the coarse reading scale on the post and a fine reading scale on the periphery of the thimble. Vertical scale index lines are scribed on the posts as shown in FIG. 5. The scale setting is read in the same manner a micrometer is read.

Figure 8:
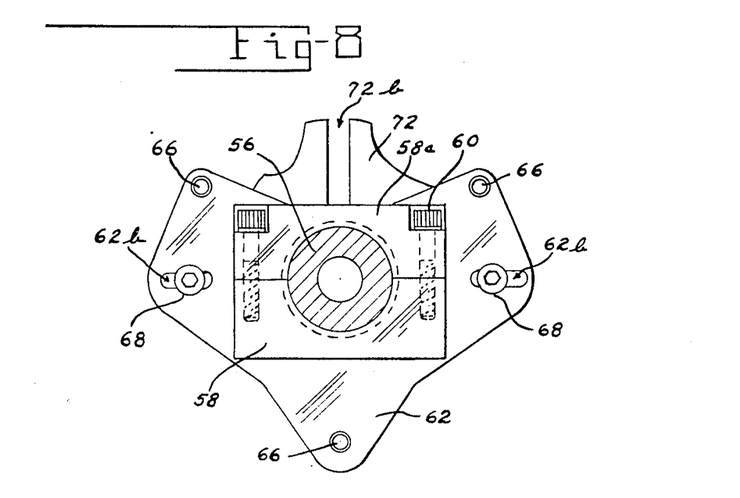
FIG. 8 is a bottom plan view taken along the line 8—8 on FIG. 2 and showing in particular the lateral movement and the ball socket permitting canting of the wobble plate.

Specific reference is made to FIG. 8 which depicts two elongated slots 62b in the lateral slide 62. Screws 68 detachably hold the lateral slide 62 against the vertical rise plate 70 (hidden in FIG. 8). The lateral slide 62 has a scale scribed to be on both sides of the 0 vertical axis of the articulator as shown in FIG. 9. The function of the lateral slide 18 on the lower mounting jig and the function of the lateral slide 62 on the upper mounting jig 40 are the same.

The vertical rise plate 70 on the upper mounting jig also performs the same function as the vertical rise plate 24 on the lower mounting jig. The vertical rise plate 70 has an index line scribed on the edge adjacent to the scale shown in FIG. 9; the index line being scribed to be on 0 when the lateral slide is on the vertical axis of the articulator.

The vertical rise plate 70 has two vertical rise plate pins 70a which are identical to the vertical rise plate pins 24a which have previously been described. The pins 70a are scribed with a scale identical to the scale on pins 24a.

The base plate 72 is identical with base plate 28 on the lower mounting jig 10. Guide sleeves 72a are also identical with guide sleeves 28a. Slot 72b in base plate 72 is identical to slot 28b in base plate 28 and engages a guide pin 5g on the underside of the pivoted leaf of the articulator as shown in FIG. 1. The retaining pin 72c attached to base plate 72 (shown in FIGS. 2, 5 and 9) is identical to the retaining pin 28c on base plate 28.

The subassembly comprising cast plate 42, wobble plate 46, lateral slide 62 and vertical rise plate 70 may be manually positioned and held in place by means of screws 74. This vertical positioning is independent of, and has no effect on any other movement.

The mounting ring 76 shown in FIGS. 2, 5 and 9 is identical with the mounting ring 32 shown in FIGS. 2, 5 and 6. If desired, a small rim may be put on the lower ring as indicated. The mounting ring 76 may be retained on the leaf of the articulator in the same manner that the mounting ring 32 is retained in the base of the articulator. The mounting ring 76 is provided with the identical elongated slot for anterior-posterior movement and with the same scale as on mounting ring 32.

Washer 78 is identical with washer 36 and functions for the same purpose. Knurled nut 80 is identical with knurled nut 38 and also functions for the same purpose. It is thus noted that the upper mounting jig provides four independent movements for the mounted dental cast; namely, vertical movement, anterior-posterior movement, lateral movement, and canting movement. Additionally, the dental cast may be rotated in the ball socket when the socket is freed from the ball by loosening screws 60.

U.S. Pat. No. 3,975,489 teaches a method for embedding threaded buttons into the base of dental casts at the time the casts are formed, but before the material from which the casts are made has set. This method will not work in cases where it is desired to embed threaded buttons after the dental casts have set.

In accordance with the teachings of the present invention, such embedded buttons may be formed by a new method not previously used in the art. This new method is to put a cavity into the base of the hardened dental cast, undercut the cavity to acquire additional mechanical retention, partially fill the cavity with a cold setting material such as the plastic used to fabricate dentures, place a screw thread into the plastic material while it is in a fluid state, allow the plastic material to harden and then remove the screw. This method will produce an embedded button which has the external appearance of a button embedded in accordance with U.S. Pat. No. 3,975,489, but which has an entirely different cross-section and is made by an entirely different method, not only in the method of forming the button, but also in the method of embedding it into the dental cast.

FIG. 13 illustrates a third species of the jig which is identified as mounting jig 82 and also illustrates the method of embedding a button in accordance with the present invention. The mounting jig 82 comprises the same mounting ring 76 which was used with the upper mounting jig 40. A mounting screw 84 having a knurled head passes through the elongated slot in the mounting ring where it is adjusted to proper vertical relationship with the dental cast and is held to such adjustment by means of two knurled lock nuts 86. Wrench tightening nuts may also be used. This mounting jig assembly may be retained in either the base or the pivoted leaf of the articulator, or both.

The embedded button 90 is formed by cutting a cavity into the base of the dental cast with a dental burr such as is used in all dental laboratories, undercutting the bottom of the cavity with a small burr, as illustrated, in order to increase the structural retention of the button, filling the cavity with a fluid cold setting material such as the plastic from which dentures are made, lowering the screw 84 into the cold setting material while it is in fluid form and allowing the cold setting material to set around the screw. It will be found that this method will form a perfect screw thread in the plastic which engages the screw with zero clearance, while at the same time the screw may repeatedly be unscrewed from and again screwed into the thread of the embedded button. Repeated tests have shown that the plastic does not adhere or bond to the metal screw.

The button may also, and has been made from other cold setting materials such as Melotte Metal which is found in dental laboratories, and from ordinary solder. These metallic materials make suitable buttons; however, plastic is the preferred material because, unlike metal, plastic does not gum the grinding discs used in dental laboratories to face grind the bases on dental casts. These grinding discs are designed for use on plaster casts and not for use on metal. It has been found that plastic material such as is used to make dentures does not have any adverse effect on such grinding discs.

Experiments were conducted to determine the feasability of embedding pre-formed buttons into casts by using adhesives. Buttons were embedded by this method; however, they are not preferred for several reasons. In the first place because of the nature of the plaster from which casts are made, accurate holes fitting the buttons could not be cut by using a hand held cutter. In the second place, the adhesive did not form a chemical bond with the plaster, and the buttons were not embedded as firmly as desired. In the third place, the bond between the adhesive and the plaster diminishes in the presence of hot water.

Experiments were also conducted to determine the feasability of drilling and tapping directly into the plaster casts. This was only partially successful and results were not consistent. It was found that threads could be formed directly into plaster dental casts if a screw was embedded into the plaster at the time the cast was being formed. The screw could be removed after the cast had set; however, the threads in the plaster were ragged and were deemed to have insufficient shear strength. In conclusion, it was found that plastic embedded buttons were the superior method of providing dental casts with screw threads which could be used for mounting dental casts in a dental articulator.

It is noted that the pre-cast buttons in accordance with U.S. Pat. No. 3,975,489 are tapered. This is to prevent the buttons from being pulled from the dental cast when the cast is being pulled from the mold in which it was poured. Experiments have shown that although such buttons could not be pulled from a dental cast short of also destroying the cast, it was possible to apply enough torque to cause the button to break loose and turn in the dental cast. The undercut in the cavity which is recommended when buttons are to be poured in accordance with the present invention serve two purposes: the undercut forms a button which cannot be pulled from the dental cast, and, since the undercut cannot be made to a uniform radius, the poured button cannot be rotated in the dental cast. As an alternative to an undercut as shown in FIG. 13, several angular detents may be cut into the cast as shown in FIG. 2. A button made in this manner can neither be pulled from nor rotated in the dental cast.

Three species of mounting jigs have been depicted and described. These jigs may be used in several combinations, primarily dependent on the manner in which the threaded buttons are to be embedded and the laboratory functions to be performed.

A review of the method of embedding buttons as taught by U.S. Pat. No. 3,975,489 will disclose that there is no provision for embedding buttons in a lower and an upper dental cast to meet the requirement that these two buttons be on a common vertical axis when the two dental casts are to be mounted in their occlusion position. Under the old method of mounting casts in an articulator, the casts are placed in their occlusion position and are then mounted by plastering them to the articulator.

When mounting dental casts in accordance with the present invention, one method is to embed buttons into the upper and lower dental casts in accordance with U.S. Pat. No. 3,975,489; to then mount them in mounting jigs such as depicted in the present FIGS. 1 and 2; and to then adjust the two dental casts to their occlusion position. This adjustment is accomplished by means of the vertical, lateral, and anterior-posterior adjustments of the two mounting jigs, and by the wobble plate adjustment on the upper mounting jig. Since the two bases of the dental casts are individually ground, the canting adjustment produced by the wobble plate compensates for any lack of parallelism between the bases of the dental casts when they are brought to the occlusion position. What small amount of rotational adjustment may be required is made by slightly loosening the cap of the ball socket on the upper mounting jig and again tightening it after the adjustment has been made.

Approximately 85% of dental laboratory work, in which dental casts are mounted in articulators, also requires the removal and replacement of the dental casts into their original positions. This is 100% true in the fabrication of removable partial dentures and complete dentures. This removal and replacement involves a relatively high risk of breaking casts when plaster is used and is also very time consuming.

When using mounting jigs in accordance with the present invention there is little if any danger of breaking casts, the casts are easily remounted to their original position, and there is a substantial time savings over the time required for plaster to become thoroughly set, during which setting time no laboratory work can be done with the mounted casts. There is no delay when the casts are mounted in accordance with the present invention.

Another combination of jigs may be used in a situation where the lower dental cast has a button embedded in accordance with U.S. Pat. No. 3,975,489 and the upper cast does not contain a button. In this situation, the lower cast may be mounted on a jig such as the lower mounting jig shown in FIGS. 1 and 2 and a mounting button may be formed in the upper cast as depicted in FIG. 13.

Although not the only method which may be used, as will be shown below, the entire upper mounting jig except the mounting ring 76 is removed from the articulator and replaced with mounting screw 84 and the lock nuts 86. If desired, the lateral and anterior-posterior adjustments on the lower mounting jig may be set to zero; however, this is not necessary.

The upper and lower casts are placed in their occlusion position after which the mounting screw 84 is lowered until the bottom end is in proximity with the base of the upper cast. This position is roughly marked, after which a cavity with undercut is cut into the base of the cast at the marked position. The cavity is freed of loose plaster dust after which the mounting screw is lowered until it touches the bottom of the cavity, after which the screw is backed out about one turn and locked into position by the two lock nuts 86. The leaf on the articulator is then swung out of its normally horizontal position which will thereby swing the mounting screw out of the cavity in the base of the dental cast. The cavity is then filled nearly full with the fluid plastic after which the leaf on the articulator is swung back to its normal position which will put the end of the mounting screw into the fluid plastic where it remains undisturbed until the plastic button has been formed by the set plastic. Since the upper and lower dental casts were in their occlusion position at the time the fluid plastic in the upper cast cavity was setting, no further adjustment is normally necessary. Any minor adjustment which may be desired can be made with the adjustments on the lower mounting jig.

If the mounting jigs, including the mounting rings 32 and 76 are made detachable from the articulator as shown, it will be easier to replace the mounting ring with an alternate mounting ring, not having an elongated slot for anterior-posterior movement, when it is desired to use mounting screw 84. The new mounting ring should be threaded on the vertical axis of the articulator to engage the mounting screw 84. This will make adjusting the mounting screw somewhat easier and will also eliminate the necessity for two lock nuts since one will suffice.

Specific reference is made to the notch 84a at the lower end of mounting screw 84 as depicted in FIG. 13. This notch which may be made with the corner of a file for example, will fill with fluid plastic to form a small ear or lip on the poured plastic button. The lip will lock the mounting screw in the plastic and will prevent any unwanted rotation of the dental cast until such time as the lip is forceably sheared or cut to remove the cast. It has been found that the notch need be only in the first screw thread and that it should be somewhat more shallow than the root of the thread. When forceably removed, the notched thread will act as a tap and will cut through the small plastic lip. If the cast is to be remounted on the mounting screw, rotation of the cast may be prevented by a lock nut such as lock nut 86.

Poured buttons may be formed in the base of any dental cast. Such poured buttons may also be embedded in a position favorable for mounting the casts on the mounting jigs depicted in FIGS. 1 and 2. For example, a transparent template of the same size as cast plates 12 and 42 may be made with a scribe hole at the center. This template may be oriented to its desired position on the cast where the center is scribed or otherwise marked through the template to mark the location of the cavity to be cut.

A second metallic duplicate of the cast plates 12 and 42 is made to be threaded at the center to receive a screw of the same size as the mounting screws 14 and 44. The screw in the metal duplicate of the cast plate may be a round head screw of such length that when the screw head is butted against the duplicate plate, the length of the protruding screw on the other side of the plate will be slightly longer than the protruding screws in the mounting jigs.

When the cast has been marked, the cavity is cut, after which the cavity is filled to proper depth with liquid plastic. The duplicate plate with the screw head in its butting position against the plate is then placed in position on the cast with the protruding screw thread entering the liquid plastic and the plastic allowed to set, after which the screw is unthreaded from the plastic button which has been embedded. The duplicate plate resting against the cast assures a perpendicular thread in the embedded button. The reason why the screw in the duplicate plate should protrude a little more than the mounting screws in the jigs is to make certain that the mounting screws in the jigs do not bottom in the embedded buttons before the dental casts are firmly mounted against the mounting plates of the jigs.

FIGS. 11 and 12 illustrate the use of a second poured embedded button 92 which is useful in establishing and maintaining the angular position of a dental cast when mounted in a jig such as depicted in FIGS. 1 and 2. The mounting button 92 may be formed by the same technique and at the same time the centrally located button 90 is formed. The transparent template is provided with a second properly located scribe hole, and a second thread forming screw is placed in the metallic duplicate of the cast plates 12 and 42. The cast plates 12 and 42 are provided with an elongated slot 94 for receiving a flat head screw 96 which engages the embedded button 92.

Another advantage of the second button 92 is that it will prevent any rotation of the dental cast in the event the centrally located screw is not affixed firmly enough when the cast is mounted on the jig. Since all the adjusting movements on the jigs can be controlled within very close tolerances, the second embedded button provides further assurance that dental casts may be removed from a jig and be remounted to their original position in the articulator.

Buttons embedded in accordance with U.S. Pat. No. 3,975,489 may often be placed into dental casts by the dentist at the time he takes impressions and pours casts. Such buttons are not always in the most desirable location for mounting the casts in the dental laboratory's articulators. It has presented no problem to relocate such buttons by the pouring technique of the present invention. It has also been found that a button need not be completely drilled out, that fresh plastic can be poured against previously set plastic, as for example, when a hole is to be moved a distance less than the radius of the original button.

Embedded buttons formed by the pouring technique of the present invention will have threads which are normal to the base of the casts when formed by use of the metallic duplicate of the cast plates of the jigs. When the buttons are formed as shown in FIG. 13, the threads will be parallel to or coaxial with the vertical axis of the articulator and will not require a canting adjustment to place the dental casts into their occlusion position because the casts were in such position at the time the plastic set. The method depicted in FIG. 13 is especially useful when fabricating fixed partial dentures, individual crowns and other work where it is not necessary to remove and remount the casts.

A mounting jig such as shown in FIG. 13 may also be substituted for the lower mounting jig shown in FIGS. 1 and 2 in situations where casts are not required to be removed until the work has been completed. The button in the lower cast may be installed in accordance with U.S. Pat. No. 3,975,489 or by the pouring technique of the present invention.

A No. 10-32 screw was found ideal for use with the embedded buttons. The nearest metric equivalent is 5 mm; however, threads of greater pitch than standard metric pitch are preferable.

Within the scope of the present invention, other uses for embedding screws having a notch as 84a in plastic are obvious. For example, access covers which are to be removed only for other than routine servicing, or in situations where certain parts are to remain in sealed relationship. The torque required to start turning a screw for its removal will indicate whether or not the lip in the plastic thread was intact or had previously been sheared.

It is to be understood that the embodiment of the present invention as shown and described is to be regarded merely as illustrative, and that the invention is susceptible to variations, modifications and changes, without regard to construction methods, within the scope of the appended claims.

We claim:

1. A method of forming a threaded aperture in the base of a hardened dental cast for use in the fabrication of a dental prosthesis, said forming method comprising the steps:
   (a) forming a cavity of suitable depth and diameter in the base of said dental cast, said cavity to be substantially perpendicular to the occlusal plane of said dental cast;
   (b) filling said cavity to a suitable depth with a fluid cold setting material;
   (c) forming a notch in at least one external thread of an elongated threaded member and inserting said member into said fluid cold setting material before it sets; and,
   (d) allowing said cold setting material to set around said elongated member and removing said member to form said threaded aperture.

2. A method of forming a threaded aperture in accordance with claim 1 in which said fluid cold setting material is a plastic.

3. A method of forming a threaded aperture in accordance with claim 1 in which said cavity is undercut to increase structural rigidity of said embedded button in said dental cast.

4. A method of forming a threaded aperture in accordance with claim 1 in which the wall of said cavity is provided with at least one outwardly extending detent to increase structural rigidity of said embedded button in said dental cast.

5. A method of forming a threaded aperture in accordance with claim 1 in which said screw thread has a longitudinal notch in at least the end thread of said screw thread and of a depth not exceeding the thread depth.

* * * * *